United States Patent
Johnson et al.

(10) Patent No.: US 8,506,767 B2
(45) Date of Patent: *Aug. 13, 2013

(54) THIN-FILM SHAPE MEMORY ALLOY DEVICE AND METHOD

(75) Inventors: A. David Johnson, San Leandro, CA (US); Valery V. Martynov, San Francisco, CA (US); Vikas Gupta, San Leandro, CA (US); Arani Bose, New York, NY (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/171,243

(22) Filed: Jun. 28, 2011

(65) Prior Publication Data

US 2011/0253525 A1 Oct. 20, 2011

Related U.S. Application Data

(60) Continuation of application No. 12/357,104, filed on Jan. 21, 2009, now Pat. No. 7,981,258, which is a continuation of application No. 11/027,814, filed on Dec. 28, 2004, now abandoned, which is a continuation of application No. 10/345,782, filed on Jan. 16, 2003, now abandoned, which is a division of application No. 09/768,700, filed on Jan. 24, 2001, now Pat. No. 6,533,905.

(60) Provisional application No. 60/177,881, filed on Jan. 24, 2000, provisional application No. 60/211,352, filed on Jun. 13, 2000.

(51) Int. Cl.
*C23C 14/35* (2006.01)

(52) U.S. Cl.
USPC .......... 204/192.15; 204/192.12; 216/41; 216/96; 216/100

(58) Field of Classification Search
USPC .......... 204/192.12, 192.15; 216/41, 96, 216/100
See application file for complete search history.

(56) References Cited

U.S. PATENT DOCUMENTS 3,668,131 A    6/1972  Banush et al.
3,991,898 A   11/1976  Hansen et al.

(Continued)

FOREIGN PATENT DOCUMENTS

WO    WO 99/62432 A1    12/1999

OTHER PUBLICATIONS

J. Busch et al., "Shape-memory properties in Ni-Ti sputter-deposited film", Dec. 15, 1990, Journal of Applied Physics, vol. 68, Issue 12 (abstract only).

(Continued)

*Primary Examiner* — Rodney McDonald
(74) *Attorney, Agent, or Firm* — Vista IP Law Group LLP

(57) ABSTRACT

A thin film device, such as an intravascular stent, is disclosed. The device is formed of a seamless expanse of thin-film (i) formed of a sputtered nitinol shape memory alloy, defining, in an austenitic state, an open, interior volume, having a thickness between 0 5-50 microns, having an austenite finish temperature $A_f$ below 37° C.; and demonstrating a stress/strain recovery greater than 3% at 37° C. The expanse can be deformed into a substantially compacted configuration in a martensitic state, and assumes, in its austenitic state, a shape defining such open, interior volume. Also disclosed is a sputtering method for forming the device.

20 Claims, 4 Drawing Sheets

(56) References Cited

U.S. PATENT DOCUMENTS

| | | | |
|---|---|---|---|
| 4,151,064 A | 4/1979 | Kuehnle | |
| 5,061,914 A | 10/1991 | Busch et al. | |
| 5,474,563 A | 12/1995 | Myler et al. | |
| 5,772,864 A | 6/1998 | Møller et al. | |
| 6,013,854 A | 1/2000 | Moriuchi | |
| 6,096,175 A * | 8/2000 | Roth | 204/192.15 |
| 6,107,004 A | 8/2000 | Donadio, III | |
| 6,169,269 B1 | 1/2001 | Maynard | |
| 6,224,626 B1 | 5/2001 | Steinke | |
| 6,358,380 B1 | 3/2002 | Mann et al. | |
| 6,379,383 B1 | 4/2002 | Palmaz et al. | |
| 6,533,905 B2 * | 3/2003 | Johnson et al. | 204/192.15 |
| 6,849,085 B2 | 2/2005 | Marton | |
| 7,981,258 B2 * | 7/2011 | Johnson et al. | 204/192.15 |

OTHER PUBLICATIONS

S. Miyazaki et al., "Martensitic Transformations in sputter-deposited Ti-Ni-Cu shape memory alloy thin films", 1996, Thin Solid Films, 281-282, Elsevier, pp. 364-367.

P. Dario et al., "Shape Memory Alloy Microactuators for Minimally Invasive Surgery", Proceedings of SMST-94 Conference, pp. 427-433, Pacific Grove, CA (1994).

A.D. Johnson, "Vacuum-Deposited TiNi Shape Memory Film; Characterization and Applications in Microdevices", J. Micromech. Microeng, 1:31-41, 1991.

P. Krulevitch et al., "Thin Film Shape Memory Alloy Microactuators", J. Micromech. Microeng. 5(4):270-282, 1996.

L.M. Schetky, "Shape-Memory Alloys", Scientific American 74-82, 1979.

Yang et al., "Transformations in sputter-deposited thin films of NiTi shape memory alloy", Materials Letters 22, Feb. 1995, pp. 137-140.

* cited by examiner

THIN-FILM SHAPE MEMORY ALLOY DEVICE AND METHOD

RELATED APPLICATION DATA

This application is a continuation of U.S. application Ser. No. 12/357,104, which was filed Jan. 21, 2009, which is a continuation of U.S. application Ser. No. 11/027,814, which was filed on Dec. 28, 2004, now abandoned, which is a continuation of U.S. application Ser. No. 10/345,782, which was filed on Jan. 16, 2003, now abandoned, which is a divisional of U.S. application Ser. No. 09/768,700, which was filed on Jan. 24, 2001, now U.S. Pat. No. 6,533,905, issued on Mar. 18, 2003, which claims priority to U.S. Provisional Application Ser. No. 60/177,881, filed on Jan. 24, 2000, and to U.S. Provisional Application Ser. No. 60/211,352, filed on Jun. 13, 2000, all of which are incorporated herein by reference in their entirety.

FIELD OF THE INVENTION

The invention herein is directed to a method of fabricating thin-film devices from a shape memory alloy, and to space-filling devices, e.g., intravascular devices, made by these methods.

REFERENCES

J. D. Busch and A. D. Johnson, Shape-memory Alloy Microactuator, U.S. Pat. No. 5,061,914; 29 Oct., 1991.

P. Krulevitch, A. P. Lee, P. B. Ramsey, J. C. Trevino, J. Hamilton, M. A. Northrup, Thin Film Shape Memory Alloy Microactuators, J. Micromech. Microeng. Vol. 5, No. 4, December 1996.

D. Johnson, Vacuum-Deposited TiNi Shape Memory Film: Characterization and Applications in Micro-Devices, J. Micromech. Microeng. Vol. 1, (1991) 34-41.

L. M. Schetky, Shape-Memory Alloys, Scientific American, November 1979, pages 74-82.

Hiroyasu Funakubo, ed., Shape Memory Alloys, Gordon and Breach Publishers, 1984 Translated by J. B. Kennedy.

P. Dario, M. C. Montesi, Shape Memory Alloy Microactuators for Minimally Invasive Surgery, Proceedings, of SMST-94 conference, Asilomar Calif., March 1994.

BACKGROUND OF THE INVENTION

Medical implants are increasing in use in minimally invasive surgery because of the improved medical results attainable. In particular, intravascular stents are used to reinforce blood vessels to promote healing and to prevent stenosis (narrowing) of blood vessels following procedures such as angioplasty. Alloys of titanium nickel (TiNi or Nitinoi shape memory alloy) are gaining popularity over more traditional metals such as stainless steel for use in medical implants because the properties of shape memory and superelasticity enable improvements in design- and methods of deployment of these devices. Demonstrated biocompatibility and novel methods of fabrication have resulted in wide acceptance of orthodontic braces, catheter guidewires, surgical tools, and implantable coronary stents.

Fabrication of stents from drawn TiNi tubes is practical only for a limited range of sizes. In particular, it has not been feasible to make stents having the flexibility and size required for delivery intravascularly through small catheters via the carotid arteries.

There is a growing demand for smaller and thinner, more flexible stents that can be surgically implanted or delivered via catheter, into small diameter, highly tortuous blood vessels. Suitably flexible structures can be fabricated of thin film (2-10 micrometers thick) shape memory alloys that are sputter deposited on a substrate and heat treated. Composition and heat treatment affect the phase transition temperature of the alloy, which in turn determines whether it exhibits shape memory or superelastic properties.

For maximum effectiveness, an intracranial device should be installed through a small diameter catheter, then changed to a pre-determined shape so as to fill a space and apply continuous outward pressure against the blood vessel wall. To accomplish this, three-dimensional shapes such as cylinders, cones, and hemispheres are required, and a shape-changing capability is highly advantageous.

SUMMARY OF THE INVENTION

The invention includes, in one embodiment, a thin film device comprising a seamless thin-film expanse (i) formed of a sputtered Nitinol shape memory alloy; (ii) defining, in an austenitic state, an open, interior volume; (iii) having a thickness between 0.5-100, preferably 2-50 microns; (iv) having an austenite finish temperature $A_f$ below 37° C.; and (v) demonstrating a stress/strain recovery greater than 3% at 37° C. The expanse can be deformed into a substantially compacted configuration in a martensitic state, and assumes, in its austenitic state, a shape defining such open, interior volume. The expanse may have, for example, a cylindrical, hemispherical or sock-like shape The device may include a skeletal member to which the expanse is attached, and these members may have a thickness greater than the thickness of the expanse. In addition, the expanse may be fenestrated with a selected pattern of openings in the thin film In another aspect, the invention includes a method of forming the thin-film device. The method includes the steps of placing in a magnetron sputtering device, a mandrel having an exposed, etchable outer layer that corresponds to the open, interior volume of the device to be formed, providing the sputtering apparatus with a TiNi alloy target composed of between 45-55% each of titanium and nickel, and sputter depositing material from the target adjacent said mandrel under low-pressure, low-oxygen conditions. During the deposition, the mandrel is moved relative to said target, to achieve substantially uniform sputter deposition over the entire exposed surface of the mandrel, and the deposition is continued until a desired sputtered film thickness between 0.5 and 100 microns, preferably 2 and 50 microns, is formed on the mandrel Following sputter deposition, the thin film on the mandrel is heated under annealing conditions. The thin-film device so formed is then released from the mandrel, typically by exposing the mandrel and deposited thin film to an etchant, under conditions effective to dissolve the outer layer of the mandrel. The mandrel's outer layer may be a separate coating formed on the mandrel surface, or the surface of the mandrel itself. The mandrel may be coated with a smooth surface such as polyimide before sputtering to ensure a continuous layer of deposited material.

The target has a preferred composition of between about 48 to 51 atomic percent nickel to 52 to 49 atomic percent titanium. Where the sacrificial layer material is chromium, aluminum, or copper, and the etchant may be a chrome etch, potassium hydroxide, and nitric acid.

The mandrel is preferably rotated during the sputtering step to achieve substantially uniform sputter deposition over the entire exposed surface of the mandrel.

In various embodiments the mandrel may be cylindrical, e.g., for producing a thin-film stent, sock-like, e.g., for producing an intravascular filter, or hemispherical, e.g., for producing a vaso-occlusive device.

The method may further include applying structural members to the mandrel, prior to depositing the thin film thereon, to form structural members in the formed device. For use in forming a fenestrated thin-film device, the method may further include forming on the annealed thin film, an resist layer containing a pattern of openings, exposing the coated thin film with a solvent under conditions effective to create fenestrations in the thin film corresponding to the pattern of openings, and removing the resist layer. The fenestrations may have dimensions and interfenestration spacings in the 10-50 micron range.

These and other objects and features of the invention will be more fully appreciated when the following detailed description n of the invention is read in conjunction with the accompanying drawings.

DETAILED DESCRIPTION OF THE INVENTION

I. Definitions

Figure 1:
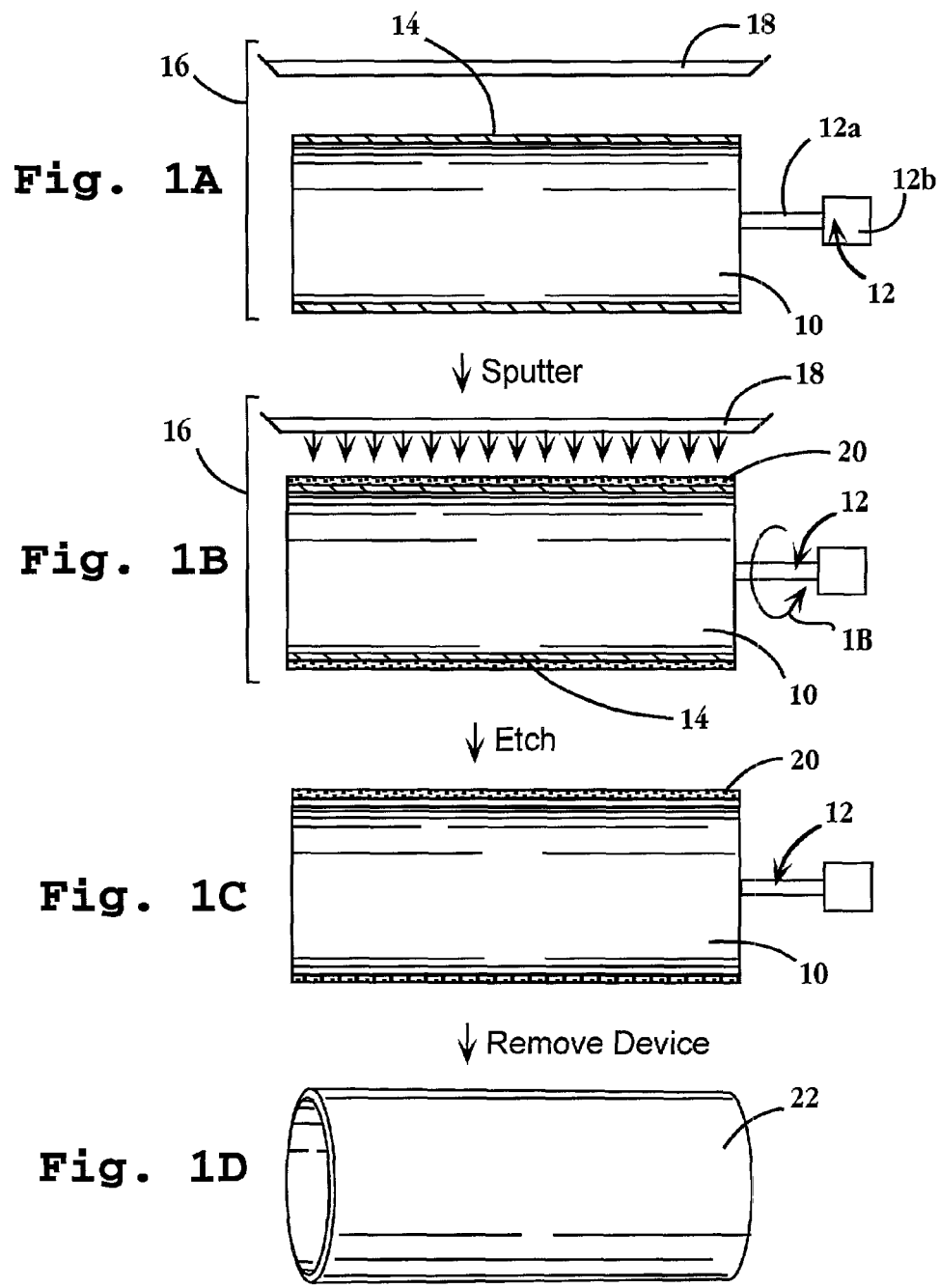
FIGS. 1A-1D illustrate steps in practicing the method of the invention.

Unless indicated otherwise, the terms below have the following meanings:

"A shape defining an open, interior volume" refers to an expanse that defines an open volume-containing space, e.g., a cylindrical, sock-like or hemispherical volume-containing space.

"Seamless thin-film expanse" means an expanse that forms an open interior volume without edge-to-edge seams.

"Nitinol" or "TiNi" refers to an alloy containing titanium and nickel, typically each between 45-55 atom percent, and optionally, other metals, such as chromium in relatively minor amount, e.g., 1-5 atom percent.

"Shape memory alloy" is an alloy that displays thermoelastic martensitic transformation defined as the ability to undergo a reversible transformation from an austenite to a martensite with a change in temperature such that an article made from such alloy has a heat stable configuration and is capable of being deformed to a heat unstable position.

"Austenitic state" refers to the stronger, higher temperature phase (crystal structure) present in a shape-memory alloy.

"Austenite finish temperature $A_f$" refers to the temperature at which a shape memory alloy finishes transforming martensite to austenite upon heating.

"Martensitic state" refers to the more deformable, lower temperature phase (crystal structure) present in a shape-memory alloy.

"Sputtered alloy" refers to an alloy formed by sputter depositing a target-material alloy on a substrate, such as a mandrel.

"Low-pressure, low-oxygen conditions" refers to sputtering conditions in which the pressure is preferably below $10^{-5}$ Torr, typically $10^{-6}$ to $10^{-8}$ Torr, and the predominant gas is an inert gas such as argon. The amount of oxygen is kept low, e.g., below 0.1 percent, by the low pressure and low oxygen content of the sputter target alloy.

"Etchable" with reference to a mandrel surface means refers to a surface layer, either part of the mandrel or a coating thereon, that can be removed by exposure to a dissolving agent, e.g., etchant.

II. Method of Forming a Thin-Film Expanse

FIGS. 1A-1D illustrate steps in forming a thin-film device in accordance with one aspect of the invention. The basic components employed in the method include a mandrel 10 having an outer exposed surface corresponding to the open, interior volume of the device to be formed The mandrel may have a variety of volume-defining surfaces, such as cylindrical, ellipsoidal, hemispherical, tapered cylindrical, and conical volume shapes, and may be constructed of a variety of materials, such as steel, glass, or silicon. The dimensions of the mandrel are dictated by the dimensions of the desired thin-film device to be formed.

The mandrel is preferably polished, and may be coated with a material such as polyimide to produce a smooth, regular surface on which to deposit shape memory alloy. In one exemplary embodiment, the mandrel is coated with a three micron thick layer of pyralin polymer resin liquid coating type PI2611 (also known as polyimide coating) obtained from HD Microsystems, by spinning the mandrel to create a thin uniform layer, curing the high-temperature polymer coating in successive steps of baking at 150° C., then curing at 250° C. and finally curing at 450-500° C. to cross-link the polymer.

The mandrel may be formed of a material that itself has an etchable surface, such as such as one formed of silicon, that can be removed upon exposure to an etchant, or may be formed of a material, such as NaCl, KCl, $NaF_2$, which are available in flat or cylindrical shapes, and which can be shaped by machining and polishing. These substrates can be dissolved directly, e.g., with an aqueous solvent, without the need of an etchable coating.

Where the mandrel is formed of a material that is itself not easily etchable, it is preferably coated with an etchable outer sacrificial layer 14, e.g., formed over a polyimide coating. Layer 14 on the mandrel is preferably metal such as chromium or other material having a highly specific etch rate relative to TiNi so that the sacrificial layer may be removed without damaging the TiNi thin film. It is preferred that the layer used not diffuse readily into TiNi during heat treatment. Alternative sacrificial layers include aluminum, copper, and photoresist such as SU8 and OCG825. An etchant such as potassium hydroxide used for etching aluminum, nitric acid used for etching copper, and Chrome Etch from Arch Chemicals Inc. containing ceric ammonium nitrate, nitric acid, and water. The etchant may be an aqueous solution for water-soluble mandrels, such as the salt mandrels noted above.

The sacrificial layer may be formed by conventional thin-film deposition means, such as vacuum thermal evaporation, electroplating, or sputtering, to form a sacrificial layer preferably less than 1 micron in thickness. In one embodiment, a chromium layer is applied to a thickness of about of 0.1 micron by the sputter deposition method detailed below, but where the target is chromium rather than a TiNi alloy.

The mandrel is mounted on mandrel holder 12 for rotation thereon in the direction of arrow 13 in FIG. 1B. The mandrel holder includes a mandrel-support rod 12a, and a motor 12b for rotating the mandrel at a desired speed, e.g., 0.5 to 2 rpms, during sputter deposition.

Also shown in the figures is a sputter deposition target 18 composed of a nickel-titanium shape-memory alloy, preferably nearly 50 atomic percent Ti, 50 atomic percent nickel, and containing minimal impurities especially carbon and oxygen. Composition control is critical to obtaining TiNi having appropriate shape memory and superelastic qualities. Increasing the content of nickel lowers the transition temperature. As little as 0.1% oxygen renders the film product brittle and unusable. The target may include minor amounts, e.g., 1-5 atomic percent, of other metals, e.g., chromium or platinum, known to effect the behavior of TiNi shape-memory alloys is specific ways.

In particular, the target is preferably selected to produce in the thin-film expanse, an austenite finish temperature $A_f$ less than 37° C. characterized by a four-point resistivity measurement in which the temperature is cycled to above 100° C. and below 0° C.; and a stress/strain recovery curve characterized by greater than 3% at 37° C. One exemplary target is composed of a nickel-titanium shape-memory alloy, preferably 46.75 weight percent Ti and 53.25 weight percent Ni, and less than 200 parts per million oxygen; formed by vacuum are melting. The alloy composition may be enriched in nickel by as much as 1-2 percent to lower the transition temperature, and heat treatment such as rapid thermal anneal followed by heat-soaking at a lowered temperature may be employed as a method of obtaining special stress-strain-temperature characteristics.

The target has exemplary diameter and thickness dimensions of 20 cm by 0.6 cm, respectively. The target is placed in the sputtering apparatus approximately 3-5 cm from the mandrel and parallel to the axis of the mandrel, as shown in FIGS. 1A and 1B.

The mandrel and target are contained in a conventional high-vacuum sputtering apparatus, indicated at 16 in FIGS. 1A and 1B. The apparatus may be any of a number of known sputtering systems that employ a direct current magnetron or radio frequency sputtering source. One exemplary apparatus is a Perkin-Elmer PE4400 series sputtering system.

In operation, the coated mandrel and target are placed in the vacuum chamber of the sputtering apparatus, and sputter deposition is carried out in a vacuum of low $10^{-7}$ Torr base pressure using a single TiNi DC magnetron target, argon gas, and a 5 kW DC power supply. High vacuum is necessary to minimize the oxygen (and other contaminants). Alternatively, the mandrel may be placed in a cylindrical magnetron sputtering system for deposition of TiNi.

Sputter deposition is carried out until a selected thickness of thin-film expanse of between 0.5-100, preferably 2-50 microns is achieved. During deposition, film thickness may be determined by measuring the time of deposition and comparing to calibrated samples that are measured by a Tencor Alpha-Step profilometer. Alternatively, film thickness may be measured by placing a piezoelectric crystal adjacent to the target and monitoring its resonant frequency during deposition.

As can be appreciated from the sputtering configuration shown in FIG. 1B, deposition onto the rotating mandrel is effective to produce a substantially uniform thickness of deposited thin film on the exposed surface of the mandrel, that is, the surface region directly exposed to the target.

When a desired film thickness is reached, the sputter deposition step is terminated, and the thin-film expanse on the mandrel is then annealed under heating/cooling conditions to achieve desired shape-memory alloy properties in the device. The annealing step may be by thermal heating or by exposure to an infrared heater in vacuum. Use of infrared heating permits rapid heating and cooling so that sacrificial layers such as aluminum may be used, and solvent-removable sacrificial layers such as photoresist. In a typical annealing process, the thin-film expanse is heated in vacuum at 500-550° C. for 20 minutes followed by gradual cooling to ambient temperature. For heat treatment the mandrel is enclosed in a stainless steel fixture to ensure uniform heating.

Following annealing, the thin-film device must be released from the mandrel. This is done preferably by exposing the mandrel and thin-film device thereon to a dissolving agent, e.g., etchant, to remove the outer mandrel layer or the sacrificial layer formed thereon. The step is shown in FIG. 1C, where sacrificial layer 14 (FIGS. 1A and 1B) is removed by the etchant. The mandrel with its two or more layers of deposits is immersed in liquid etchant at room temperature and allowed to soak until the TiNi layer is freed from the surface. The time may vary from one to 24 hours depending on the degree of fenestration of the TiNi, the thickness of the sacrificial layer, and the degree of agitation applied to the mandrel. Ultrasonic power may be used to accelerate action of the etchant.

At the end of the etching period, the coated mandrel is washed and the thin-film expanse is removed from the mandrel. This step is shown in FIG. 1D, showing a thin-film stent 22 formed in accordance with the method.

For many applications it will be desirable to form a pattern of openings or fenestrations in the thin-film device, such as will be described below with respect to FIG. 12. According to an important feature of the invention, the method of producing a thin-film device can be extended to produce microsized, precisely shaped and spaced openings or in the film. In this embodiment, fenestration patterns are selectively etched in TiNi thin film, either before or after the above annealing step, to enhance mechanical flexibility of the film, to permit fluid to flow through, to increase the expansion rate of the device or achieve improved adhesion to vascular-wall structure. A positive photoresist is spun on the thin film/silicon mandrel. One preferred photoresist material is Olin OCG825; other suitable materials are available from alternative vendors. The photoresist and thin film TiNi is then photo-lithographically patterned and etched, respectively. The etchant is, for example, a mixture of nitric acid and buffered oxide etch containing hydrogen fluoride. Fenestrations as small as 25 microns.times.25 microns in the film have been created. More generally, fenestrations and spacing between adjacent fenestrations may have dimensions in the 5-50 micron size range or larger.

In another embodiment, the method is adapted to produce a thin-film device having internal ribs or struts. In this embodiment, the coated mandrel is first provided with structural members or ribs applied or deposited on the coated surface, to serve as structural members in a thin-film device as illustrated below in FIG. 7. The structural members are preferably deposited or placed circumferentially about the coated mandrel at one or more positions along the mandrel. The ribs may be, for example, nickel/titanium wire or strips, or some other metal or polymer materials upon which a thin-film expanse can be deposited. The surface must be coated or polished to a sub-micron finish for TiNi to be successfully sputtered onto the mandrel after placement of rib structure.

III. Properties of the Thin-Film Expanse

Narrow strips of thin film prepared as above were prepared for transformation temperature measurements and stress-strain measurements. To measure transformation temperature, each thin film sample was heated and cooled while changes in voltage were measured and recorded using a 4-probe constant-current technique to produce temperature versus resistivity data.

Figure 2:
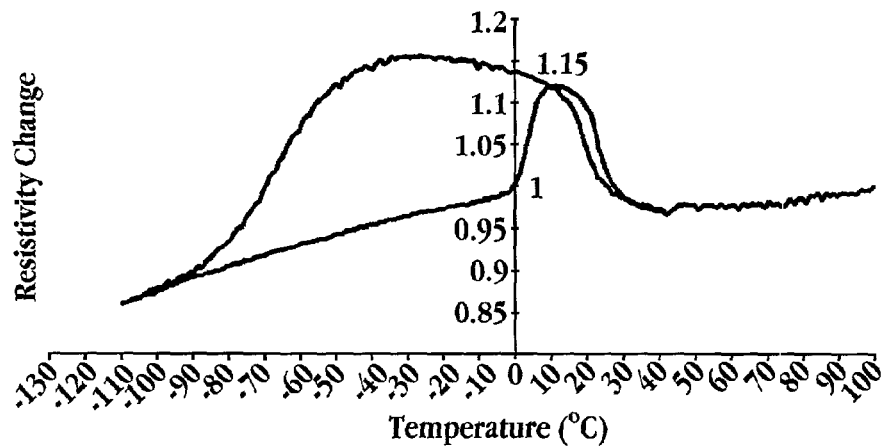
FIG. 2 shows a resistivity versus temperature curve of a TiNi thin-film expanse formed in accordance with the invention.

FIG. 2 shows a typical resistivity versus temperature curve of a TiNi film. The transformation temperatures of the alloy are as follows:

| | |
|---|---|
| Martensite start ($M_s$) | −30° C. |
| Martensite finish ($M_f$) | −80° C. |
| Austenite start ($A_s$) | 0° C. |
| Austenite finish ($A_f$) | 12-15° C. |

Since the $A_f$ of this thin film alloy is below body temperature, it is well suited to medical devices that are actuated within the blood vessel.

In stress-strain measurements, film samples 20 mm.times.1 mm.times.5 microns in size were used. The deformation fixture used allowed the deformation at a constant temperature in the temperature range from −50° C. to +90° C. by immersion in an alcohol or water bath. The force applied to the sample and the sample elongation was measured respectively by a strain gage and an LVDT connected to a computer. LABVIEW™ software was used for collecting the data and plotting the stress-strain and resistivity graphs.

Figure 3:
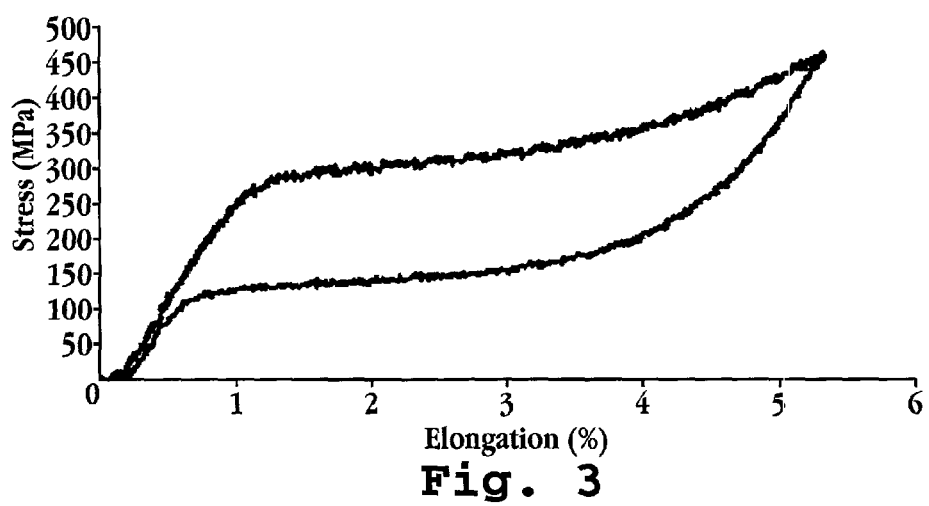
FIG. 3 illustrates a stress-strain curve for TiNi thin film at 37° C.

FIG. 3 illustrates a stress-strain curve for TiNi thin film at 38° C. The loading plateau for the film is at about 300 MPa (~45 kpsi) and unloading plateau is at about 150 MPa (~22 kpsi). The thin film clearly exhibits superelastic behavior at body temperature that makes this an excellent material for medical devices, particular miniature implantable devices.

IV. Exemplary Devices

In another aspect, the invention includes a device formed of a seamless thin-film expanse, in accordance with the method above. The "seamless" feature refers to the fact that the expanse forms a continuous surface without interior edges. The important features of devices formed in accordance with the above method are as follows:

The devices are formed of a sputtered nitinol shape memory alloy. The expanse is formed by sputtering a thin film from a titanium/nickel alloy target, as described above. The thin-film material defines, in an austenitic state, an open, interior volume. The open interior volume is the volume of the space defined by the interior of the expanse. The expanse in the device has a film thickness of between 0.5 and 1001 microns, preferably 2-50 microns, more preferably 5-50 microns, and a substantially uniform in thickness and composition throughout the expanse. The thin-film expanse has an austenite finish temperature $A_f$ below 37° C. and demonstrates a stress/strain recovery greater than 3% at 37° C., where the expanse can be deformed into a substantially compacted configuration in a martensitic state.

Figure 4:
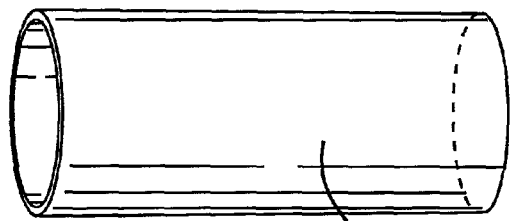
FIG. 4 illustrates a thin-film solid-wall stent constructed in accordance with an embodiment of the invention.
Figure 5:
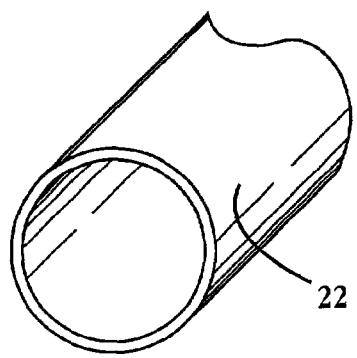
FIGS. 5 and 6 illustrate open and folded states of the stent of FIG. 4, respectively, as seen in front-on view.
Figure 6:
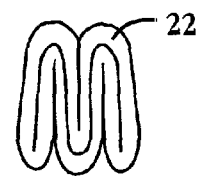

One exemplary device is shown in FIGS. 4-6, where a cylindrical thin-film expanse forms an intraluminal a stent 22. The stent has typical dimensions of about 5-75 microns film thickness, 5-50 mm in length, and 1-10 mm in diameter, in its open conditions shown in FIGS. 4 and 5. A compacted or "folded" configuration is illustrated in FIG. 6, showing stent 22 in a front-on view. As seen, the dimensions of the stent have been reduced considerably in the compacted configuration, allowing the stent, for example, to be delivered through a catheter to a vascular site in need of a stent, e.g., in a compacted, stress-induced martensite form. Upon release of the stent from the catheter at the target site, the stent regains its fully austenitic, open form, with its outer surface impinging against the walls of the vessel.

Figure 7:
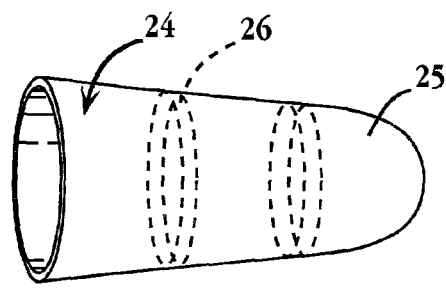
FIG. 7 illustrates a sock-like thin-film device formed in accordance with another embodiment of the invention
Figure 8:
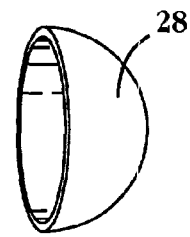
FIG. 8 illustrates a hemispherical device formed in accordance with still another embodiment of the invention.

A variety of other devices or articles are encompassed by the invention. Shown in FIG. 7 is a sock-like device 24 formed of a thin-film expanse 25 and supported internally by structural members 26. The structural ribs may be disposed in a circumferential direction, as shown, or in a longitudinal direction, like the struts in an umbrella. This device can be formed as described above, on a cone-shaped mandrel, where the mandrel is first coated prior to sputtering the thin-film expanse, and the structural members are formed on the mandrel prior to sputtering. The device may be fenestrated, as illustrated in FIG. 9, and may have a wire or other guide structure attached, for example, for pulling the device through an internal vessel, where the device acts like a filter.

In another embodiment the device is a hemispherical cap device 30, e.g., for use as a vaso-occlusive agent for treating an aneurysm. Also as discussed above, the thin-film device may be further etched, e.g., by photolithographic etching, to produce a device, such as stent 32 in FIG. 9, having defined-shape, size and position fenestrations. Fenestration patterns as small as 25 microns.times.25 microns have been etched in the film using photolithographic techniques.

Figure 9:
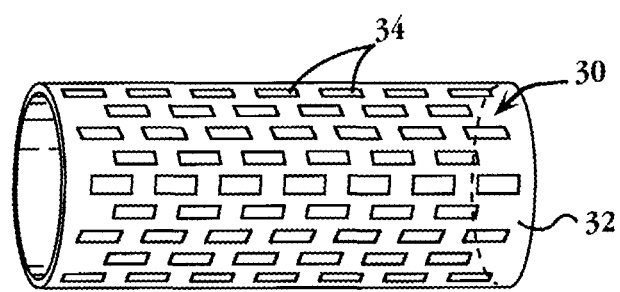
FIG. 9 illustrates a stent with a fenestrated thin-film expanse formed in accordance with the invention.

FIG. 9 shows a TiNi thin film stent 30 formed of a thin-film expanse 32 having fenestrations or windows, such as windows 34, formed therein. Windows 25 microns×25 microns with spacing of about 10 microns between the adjacent openings has been achieved. Since fenestrations are produced by using photolithographic technique, very precise, clean and sharp edges can be achieved. The ability to etch micrometer scale features with an excellent etching quality allows for the production of devices such as implantable filters, or drug-release devices.

While the invention has been described with reference to particular embodiments and conditions, it will be appreciated that a variety of changes and modifications may be made without departing from the scope of the invention.

What is claimed is:
1. A method of forming a thin-film device, comprising:
placing a mandrel in a magnetron sputtering device, the mandrel having an etchable outer surface layer;
disposing a plurality of structural members on the outer mandrel surface layer;
sputter depositing material from an TiNi alloy target to the mandrel while moving the mandrel relative to the TiNi alloy target to thereby achieve substantially uniform sputter deposition of the TiNi alloy over the outer surface layer of the mandrel, until a layer of TiNi alloy having a desired thickness is deposited on the outer surface layer of the mandrel, with the structural members being embedded in the deposited layer of TiNi alloy; and
heating to thereby anneal the deposited layer of TiNi alloy on the mandrel.

2. The method of claim 1, wherein the sputter depositing occurs under conditions including a pressure below $10^{-5}$ Torr and an amount of oxygen which is below 0.1 percent.

3. The method of claim 1, further comprising
exposing the mandrel and deposited layer of TiNi alloy to an etchant under conditions effective to remove the outer surface layer of the mandrel, the deposited layer of TiNi alloy and embedded structural members forming a thin-film device, and
removing the thin-film device so formed from the mandrel.

4. The method of claim 1, wherein the TiNi alloy target has a composition of between about 48 to 51 atomic percent nickel.

5. The method of claim 3, wherein the outer surface layer of the mandrel is formed from a material selected from the group consisting of chromium, aluminum, and copper, and the etchant is selected from the group consisting of chrome etch, potassium hydroxide, and nitric acid.

6. The method of claim 1, wherein the mandrel is rotated during the sputtering.

7. The method of claim 1, wherein the outer surface layer of the mandrel has a shape selected from the group consisting of (i) cylindrical, (ii) sock-like, and (iii) hemispherical.

8. The method of claim 1, wherein the depositing is carried out until the deposited TiNi alloy layer has a thickness of between 2 to 50 microns.

9. The method of claim 1, wherein the thin-film device is a fenestrated thin-film device, the method further comprising
forming on the annealed layer of TiNi alloy a resist layer containing a pattern of openings, and
exposing the layer of TiNi alloy and resist layer to an etchant under conditions effective to create fenestrations in the layer of TiNi alloy corresponding to the pattern of openings.

10. The method of claim 9, wherein the fenestrations have dimensions and interfenestration spacings of between about 10-50 microns.

11. The method of claim 1, wherein the thin-film device has an austenitic finish temperature $A_f$ below 37° C.

12. The method of claim 11, wherein the thin-film device is characterized by a four-point resistivity measurement in which the temperature is cycled to above 100° C. and below 0° C.

13. The method of claim 1, wherein the deposited layer of TiNi alloy on the mandrel is heated in a vacuum at 500-550° C.

14. The method of claim 1, wherein the material from the TiNi alloy target is sputter deposited to the mandrel under conditions including a pressure below $10^{-5}$ Torr, an inert predominant gas, and an amount of oxygen which is below 0.1 percent.

15. A method of forming a thin-film device, comprising:
forming an etchable outer surface layer on a mandrel;
disposing a plurality of structural members on the mandrel outer surface layer;
sputter depositing material from an TiNi alloy target to the mandrel while moving the mandrel relative to the TiNi alloy target to thereby achieve substantially uniform sputter deposition of the TiNi alloy over the outer surface layer, until a layer of TiNi alloy having a desired thickness is deposited on the outer surface layer, with the structural members being embedded in the deposited layer of TiNi alloy; and
heating to thereby anneal the deposited layer of TiNi alloy on the mandrel.

16. The method of claim 15, further comprising coating the mandrel with a polyimide layer before forming the etchable outer surface layer on the mandrel, so that the etchable outer surface layer is formed on the polyimide layer.

17. A method of forming a fenestrated thin-film device, comprising:
placing a mandrel in a magnetron sputtering device, the mandrel having a polyimide layer and an etchable sacrificial outer surface layer disposed on the polyimide layer;
sputter depositing material from TiNi alloy target onto the sacrificial outer surface layer of the mandrel while moving the mandrel relative to the TiNi alloy target to thereby achieve substantially uniform sputter deposition of the TiNi alloy over the outer surface layer of the mandrel until a layer of TiNi alloy having a desired thickness is deposited on the outer surface layer of the mandrel;
heating to thereby anneal the deposited layer of TiNi alloy on the mandrel;
forming on the annealed layer of TiNi alloy, a resist layer containing a pattern of openings; and
exposing the layer of TiNi alloy and the resist layer to an etchant under conditions effective to create fenestrations in the layer of TiNi alloy corresponding to the pattern of openings.

18. The method of claim 17, wherein the fenestrations have dimensions and interfenestration spacings of between about 10-50 microns.

19. The method of claim 17, wherein the sputter depositing occurs conditions including a pressure below $10^{-5}$ Torr and an amount of oxygen which is below 0.1 percent.

20. The method of claim 17, further comprising
exposing the mandrel and deposited layer of TiNi alloy to a second etchant, under conditions effective to remove the outer surface of the mandrel, and
removing the thin-film device so formed from the mandrel.

* * * * *